US010702204B2

(12) United States Patent
Vining

(10) Patent No.: US 10,702,204 B2
(45) Date of Patent: *Jul. 7, 2020

(54) APPARATUS AND METHOD FOR USE IN ANALYZING A PATIENT'S BOWEL

(71) Applicant: UNIVERSITY OF MARYLAND, BALTIMORE, Baltimore, MD (US)

(72) Inventor: David J. Vining, Houston, TX (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/139,601

(22) Filed: Sep. 24, 2018

(65) Prior Publication Data

US 2019/0021648 A1 Jan. 24, 2019

Related U.S. Application Data

(63) Continuation of application No. 14/459,365, filed on Aug. 14, 2014, now Pat. No. 10,092,234, which is a
(Continued)

(51) Int. Cl.
*A61B 5/00* (2006.01)
*A61B 5/03* (2006.01)
(Continued)

(52) U.S. Cl.
CPC .............. *A61B 5/4255* (2013.01); *A61B 5/03* (2013.01); *A61B 5/036* (2013.01); *A61B 5/4824* (2013.01);
(Continued)

(58) Field of Classification Search
CPC .............. A61B 10/04; A61B 17/00234; A61B 1/00119; A61B 1/015
(Continued)

(56) References Cited

U.S. PATENT DOCUMENTS 2,539,189 A * 1/1951 Garrett .................. A61M 31/00
137/596
3,374,762 A 3/1968 Baldwin
(Continued)

FOREIGN PATENT DOCUMENTS

CN 102334973 2/2012
DE 4219859 12/1993
(Continued)

OTHER PUBLICATIONS

International Search Report and Written Opinion for Application No. PCT/2011/061824 dated Feb. 9, 2012.
(Continued)

*Primary Examiner* — May A Abouelela
(74) *Attorney, Agent, or Firm* — Donald R. Piper, Jr.; Dann, Dorfman, Herrell & Skillman, P.C.

(57) ABSTRACT

An apparatus and method are provided for use in studying a patient's bowel which combines recording and analysis of physiologic parameters and patient sensory perception. A pain input detector, a pain transducer, and a processor are provided. A gas pressure transducer and flow meter may also be provided. Output data may be generated to reflect perceived patient pain, volume of gas delivered to the patient's bowel, and bowel pressure. An indication of perceived patient pain is processed by the processor to generate data that may used to validate a scan of a patient or may be used as a diagnostic tool.

16 Claims, 6 Drawing Sheets

Related U.S. Application Data continuation of application No. 12/682,963, filed as application No. PCT/US2008/079826 on Oct. 14, 2008, now abandoned.

(60) Provisional application No. 60/979,962, filed on Oct. 15, 2007.

(51) Int. Cl.
*A61M 13/00* (2006.01)
*G06F 19/00* (2018.01)
*A61B 5/055* (2006.01)
*A61B 6/03* (2006.01)

(52) U.S. Cl.
CPC ......... *A61B 5/7475* (2013.01); *A61M 13/003* (2013.01); *G06F 19/00* (2013.01); *A61B 5/0073* (2013.01); *A61B 5/055* (2013.01); *A61B 6/03* (2013.01); *A61M 2205/3334* (2013.01); *A61M 2205/3344* (2013.01); *A61M 2205/502* (2013.01); *A61M 2205/581* (2013.01); *A61M 2205/582* (2013.01); *A61M 2205/583* (2013.01); *A61M 2210/1064* (2013.01); *A61M 2230/63* (2013.01)

(58) Field of Classification Search
USPC ............. 600/587, 595, 561, 560; 340/573.1; 604/23
See application file for complete search history.

(56) References Cited

U.S. PATENT DOCUMENTS

| | | | |
|---|---|---|---|
| 3,674,010 A * | 7/1972 | Falenks | A61B 1/00082 600/109 |
| 3,858,572 A | 1/1975 | Binard | |
| 3,867,941 A | 2/1975 | Lindemann | |
| 3,870,072 A | 3/1975 | Lindemann | |
| 3,940,237 A | 2/1976 | Gonzalez | |
| 3,943,938 A | 3/1976 | Wexler | |
| 3,985,533 A | 10/1976 | Grossman | |
| 4,013,076 A | 3/1977 | Puderbaugh | |
| 4,019,515 A | 4/1977 | Kornblum | |
| 4,030,500 A | 6/1977 | Ronnquist | |
| 4,048,992 A | 9/1977 | Lindemann | |
| 4,052,986 A | 10/1977 | Scaife | |
| 4,090,502 A | 5/1978 | Tajika | |
| 4,117,847 A | 10/1978 | Clayton | |
| 4,182,332 A | 1/1980 | Delaney | |
| 4,207,887 A | 6/1980 | Hiltebrandt | |
| 4,260,496 A | 4/1981 | Beer | |
| 4,276,874 A | 7/1981 | Wolvek | |
| 4,391,280 A | 7/1983 | Miller | |
| 4,419,099 A | 12/1983 | Miller | |
| 4,429,693 A | 2/1984 | Blake | |
| 4,448,207 A | 5/1984 | Parrish | |
| 4,464,169 A | 8/1984 | Semm | |
| 4,504,270 A | 3/1985 | Miller | |
| 4,554,078 A | 11/1985 | Huggins | |
| 4,637,814 A | 1/1987 | Leiboff | |
| 4,664,114 A | 5/1987 | Ghodsian | |
| 4,676,774 A | 6/1987 | Semm | |
| 4,682,979 A | 7/1987 | Girouard | |
| 4,687,002 A | 8/1987 | Lahr | |
| 4,734,109 A | 3/1988 | Cox | |
| 4,758,221 A | 7/1988 | Jureidini | |
| 4,795,429 A | 1/1989 | Feldstein | |
| 4,865,018 A | 9/1989 | Kanno | |
| 4,874,362 A * | 10/1989 | Wiest | A61M 13/003 604/26 |
| 4,875,899 A | 10/1989 | Holtermann | |
| 4,883,462 A * | 11/1989 | Williamson | A61H 9/0078 604/540 |
| 4,902,484 A | 2/1990 | Martin | |
| 4,917,692 A | 4/1990 | Steer | |
| 4,930,997 A | 6/1990 | Bennett | |
| 4,946,720 A | 8/1990 | Oishi | |
| 4,957,486 A | 9/1990 | Davis | |
| 4,971,034 A * | 11/1990 | Doi | A61B 1/00068 600/104 |
| 5,006,109 A * | 4/1991 | Douglas | A61M 13/003 600/560 |
| 5,019,059 A | 5/1991 | Goldberg | |
| 5,029,580 A | 7/1991 | Radford | |
| 5,061,239 A | 10/1991 | Shiels | |
| 5,084,060 A * | 1/1992 | Freund | A61M 25/1018 604/920 |
| 5,098,375 A | 3/1992 | Baier | |
| 5,102,416 A | 4/1992 | Rock | |
| 5,131,906 A | 7/1992 | Chen | |
| 5,160,325 A | 11/1992 | Nichols | |
| 5,176,629 A | 1/1993 | Kullas | |
| 5,176,630 A | 1/1993 | Shilling | |
| 5,178,606 A | 1/1993 | Ognier | |
| 5,184,074 A | 2/1993 | Arakawa | |
| 5,196,244 A | 3/1993 | Beck | |
| 5,292,304 A | 3/1994 | Mantell | |
| 5,312,343 A | 5/1994 | Krog | |
| 5,322,070 A | 6/1994 | Goodman | |
| 5,328,458 A | 7/1994 | Sekino | |
| 5,330,486 A | 7/1994 | Wilk | |
| 5,360,396 A | 11/1994 | Chan | |
| 5,364,363 A | 11/1994 | Pearson | |
| 5,365,928 A | 11/1994 | Rhinehart | |
| 5,382,229 A | 1/1995 | Grabenkort | |
| 5,383,456 A | 1/1995 | Arnold | |
| 5,405,319 A | 4/1995 | Abell | |
| 5,411,474 A * | 5/1995 | Ott | A61M 13/003 600/560 |
| 5,423,741 A | 6/1995 | Frank | |
| 5,439,441 A | 8/1995 | Grimsley | |
| 5,487,376 A | 1/1996 | Yabe | |
| 5,549,546 A | 8/1996 | Schneider | |
| 5,569,216 A | 10/1996 | Kim | |
| 5,676,155 A | 10/1997 | Novak | |
| 5,678,568 A | 10/1997 | Uchikubo | |
| 5,688,256 A | 11/1997 | Surratt | |
| 5,720,717 A | 2/1998 | D Andrea | |
| 5,779,662 A | 7/1998 | Berman | |
| 5,788,688 A | 8/1998 | Bauer | |
| 5,800,381 A | 9/1998 | Ognier | |
| 5,800,493 A * | 9/1998 | Stevens | A61B 18/08 606/28 |
| 5,817,124 A | 10/1998 | Karell | |
| 5,897,525 A | 4/1999 | Dey | |
| 5,978,697 A | 11/1999 | Maytal | |
| 5,992,419 A | 11/1999 | Sterzer | |
| 6,004,509 A | 12/1999 | Dey | |
| 6,026,684 A * | 2/2000 | Calder | A63B 21/028 73/379.02 |
| 6,059,717 A | 5/2000 | Dabney | |
| 6,066,139 A | 5/2000 | Ryan | |
| 6,068,609 A | 5/2000 | Ott | |
| 6,083,162 A * | 7/2000 | Vining | G06T 7/0012 128/920 |
| 6,136,292 A | 10/2000 | Pettersson | |
| RE36,994 E | 12/2000 | Anderberg | |
| 6,193,649 B1 | 2/2001 | Takami | |
| 6,228,048 B1 | 5/2001 | Robbins | |
| 6,261,227 B1 | 7/2001 | Takahashi | |
| 6,272,366 B1 | 8/2001 | Vining | |
| 6,299,592 B1 * | 10/2001 | Zander | A61M 13/003 600/560 |
| 6,315,716 B1 | 11/2001 | Takami | |
| 6,328,690 B1 | 12/2001 | Takami | |
| 6,400,157 B1 | 6/2002 | Bonanni | |
| 6,402,688 B1 | 6/2002 | Takami | |
| 6,402,714 B1 * | 6/2002 | Kraft-Kivikoski | A61M 13/003 600/560 |
| 6,407,308 B1 | 6/2002 | Roe | |
| 6,433,939 B2 | 8/2002 | Enomoto | |

(56) References Cited

U.S. PATENT DOCUMENTS

| | | | |
|---|---|---|---|
| 6,458,093 B1 | 10/2002 | Gord | |
| 6,467,775 B1 | 10/2002 | Denzinger | |
| 6,471,638 B1 | 10/2002 | Chang | |
| 6,473,943 B1 | 11/2002 | Thacker | |
| 6,478,782 B1 | 11/2002 | Wada | |
| 6,485,412 B1 | 11/2002 | Byrne | |
| 6,554,780 B1* | 4/2003 | Sampson | A61B 18/00 600/560 |
| 6,563,633 B2 | 5/2003 | Nakamura | |
| 6,632,194 B1 | 10/2003 | Mehner | |
| 6,682,479 B1 | 1/2004 | Takahashi | |
| 6,824,539 B2 | 11/2004 | Novak | |
| 6,866,654 B2 | 3/2005 | Callan | |
| 6,950,691 B2 | 9/2005 | Uchikubo | |
| 6,975,968 B2 | 12/2005 | Nakamitsu | |
| 7,035,681 B2* | 4/2006 | Johnson | A61B 6/481 424/9.51 |
| 7,063,670 B2 | 6/2006 | Sampson | |
| 7,066,173 B2* | 6/2006 | Banner | A61B 5/0205 128/204.23 |
| 7,147,627 B2 | 12/2006 | Kim | |
| 7,148,887 B2* | 12/2006 | Kaufman | G06K 9/209 345/419 |
| 7,149,564 B2 | 12/2006 | Vining | |
| 7,250,035 B1 | 7/2007 | Ott | |
| 7,272,430 B2 | 9/2007 | Uchikubo | |
| 7,320,599 B2* | 1/2008 | Morris | G09B 23/285 434/262 |
| 7,361,170 B2 | 4/2008 | Williams | |
| 7,476,213 B2 | 1/2009 | Uesugi | |
| 7,485,114 B2 | 2/2009 | Stiller | |
| 7,485,115 B2 | 2/2009 | Nakamura | |
| 7,549,421 B2 | 6/2009 | Levi | |
| 7,569,027 B2 | 8/2009 | Uesugi | |
| 7,654,975 B2 | 2/2010 | Mantell | |
| 7,704,223 B2 | 4/2010 | Mantell | |
| 7,722,559 B2* | 5/2010 | Uesugi | A61M 13/003 600/560 |
| 7,806,850 B2 | 10/2010 | Williams, Jr. | |
| 7,918,816 B2 | 4/2011 | Ott | |
| 7,931,588 B2* | 4/2011 | Sarvazyan | A61B 1/00147 600/117 |
| 7,938,793 B2 | 5/2011 | Mantell | |
| 7,981,072 B2* | 7/2011 | Uesugi | A61M 13/003 600/560 |
| 8,057,448 B2 | 11/2011 | Williams | |
| 8,157,763 B2 | 4/2012 | Williams, Jr. | |
| 8,414,550 B2 | 4/2013 | Roberts | |
| 2001/0037063 A1 | 11/2001 | Albert | |
| 2001/0044576 A1 | 11/2001 | Vining | |
| 2002/0045153 A1* | 4/2002 | Kaufman | G06K 9/209 434/262 |
| 2002/0161304 A1* | 10/2002 | Eide | A61B 5/021 600/485 |
| 2002/0169415 A1 | 11/2002 | Staats | |
| 2002/0193687 A1 | 12/2002 | Vining | |
| 2003/0093503 A1 | 5/2003 | Yamaki | |
| 2003/0145849 A1 | 8/2003 | Drinan | |
| 2003/0158499 A1* | 8/2003 | Smith | A61B 10/0051 600/573 |
| 2004/0030367 A1 | 2/2004 | Yamaki | |
| 2004/0059393 A1* | 3/2004 | Policker | A61K 49/0004 607/40 |
| 2004/0102731 A1 | 5/2004 | Blackhurst | |
| 2004/0138586 A1* | 7/2004 | Ganz | A61B 5/036 600/560 |
| 2004/0193045 A1 | 9/2004 | Scarborough | |
| 2004/0230157 A1 | 11/2004 | Perry | |
| 2005/0038374 A1 | 2/2005 | Williams | |
| 2005/0097191 A1 | 5/2005 | Yamaki | |
| 2005/0107766 A1 | 5/2005 | Ott | |
| 2005/0137529 A1 | 6/2005 | Mantell | |
| 2005/0222491 A1 | 10/2005 | Noda | |
| 2005/0222534 A1 | 10/2005 | Uesugi | |
| 2005/0222535 A1* | 10/2005 | Uesugi | A61B 1/00039 604/26 |
| 2005/0245803 A1 | 11/2005 | Glenn, Jr. | |
| 2006/0004322 A1 | 1/2006 | Uesugi | |
| 2006/0030751 A1 | 2/2006 | Uesugi | |
| 2006/0047184 A1 | 3/2006 | Banik | |
| 2006/0052661 A1 | 3/2006 | Gannot | |
| 2006/0055544 A1* | 3/2006 | Morguelan | G08B 1/08 340/573.1 |
| 2006/0058617 A1 | 3/2006 | Sano | |
| 2006/0079758 A1 | 4/2006 | Susi | |
| 2006/0089571 A1* | 4/2006 | Gertner | A61B 17/0401 600/593 |
| 2006/0100500 A1 | 5/2006 | Williams, Jr. | |
| 2006/0129087 A1* | 6/2006 | Uesugi | A61M 13/003 604/26 |
| 2006/0253098 A1* | 11/2006 | Garabet | A61M 31/00 604/505 |
| 2006/0257008 A1 | 11/2006 | Nolle | |
| 2007/0106209 A1 | 5/2007 | Williams, Jr. | |
| 2007/0112299 A1 | 5/2007 | Smit | |
| 2007/0163585 A1 | 7/2007 | Uesugi | |
| 2007/0179432 A1 | 8/2007 | Bar Or | |
| 2007/0244363 A1* | 10/2007 | Sano | A61B 1/00039 600/158 |
| 2007/0244424 A1 | 10/2007 | Hameed | |
| 2007/0255165 A1* | 11/2007 | Uesugi | A61B 1/00135 600/560 |
| 2007/0265492 A1 | 11/2007 | Sonnenschein | |
| 2007/0282219 A1* | 12/2007 | Holte | A61B 5/036 600/561 |
| 2007/0293734 A1 | 12/2007 | Coste-Maniere | |
| 2008/0133602 A1 | 6/2008 | Tashiro | |
| 2009/0036749 A1 | 2/2009 | Freiburger | |
| 2009/0048506 A1* | 2/2009 | Fong-Ichimura | A61B 5/055 600/411 |
| 2009/0143644 A1 | 6/2009 | Stiller | |
| 2009/0203995 A1* | 8/2009 | Matonick | A61M 25/1011 600/435 |
| 2010/0022834 A1 | 1/2010 | Noda | |
| 2010/0106080 A1 | 4/2010 | Uesugi | |
| 2010/0114011 A1 | 5/2010 | Herrmann | |
| 2010/0130917 A1 | 5/2010 | Sezeur | |
| 2010/0185139 A1 | 7/2010 | Stearns | |
| 2010/0228100 A1 | 9/2010 | Vining | |
| 2010/0268153 A1 | 10/2010 | Mantell | |
| 2010/0268154 A1 | 10/2010 | Vining | |
| 2011/0030678 A1 | 2/2011 | Power | |
| 2011/0034862 A1 | 2/2011 | Williams, Jr. | |
| 2011/0060272 A1 | 3/2011 | Iranitalab | |
| 2011/0066078 A1* | 3/2011 | Sarvazyan | A61B 5/16 600/587 |
| 2011/0263939 A1 | 10/2011 | Kaye | |
| 2012/0016293 A1 | 1/2012 | Hayashi | |
| 2012/0130304 A1 | 5/2012 | Barish | |
| 2012/0157770 A1 | 6/2012 | Williams, Jr. | |
| 2013/0102882 A1 | 4/2013 | Williams, Jr. | |

FOREIGN PATENT DOCUMENTS

| | | |
|---|---|---|
| DE | 9218373 | 3/1994 |
| EP | 0569241 | 11/1993 |
| EP | 1101506 | 5/2001 |
| FR | 2673524 | 9/1992 |
| JP | H0217141 | 2/1990 |
| JP | 427943 | 3/1992 |
| JP | 492249 | 8/1992 |
| JP | H07265261 | 10/1995 |
| JP | 9038092 | 2/1997 |
| JP | 4133845 | 10/2004 |
| JP | 2006014961 | 1/2006 |
| JP | 4297219 | 3/2006 |
| JP | 4843279 | 3/2007 |
| JP | 2008093489 | 4/2008 |
| JP | 5154094 | 9/2008 |
| JP | 2009512535 | 3/2009 |
| JP | 5344950 | 9/2010 |
| JP | 2010227484 | 10/2010 |

(56) References Cited

FOREIGN PATENT DOCUMENTS

| | | |
|---|---|---|
| JP | 2017075396 | 4/2017 |
| WO | 2005120329 | 12/2005 |
| WO | 2006002635 | 1/2006 |
| WO | 2007050516 | 5/2007 |
| WO | 2008053485 | 5/2008 |
| WO | 2009052100 | 4/2009 |
| WO | 2012071399 | 5/2012 |

OTHER PUBLICATIONS

International Search Report and Written Opinion of the Searching Authority for Application No. PCT/US05/46561; dated Sep. 13, 2007.
International Search Report and Written Opinion for Application No. PCT/US2013/032005 dated Jun. 18, 2013.
International Search Report and Written Opinion for Application No. PCT/US2006/041291 dated Sep. 13, 2007.
International Search Report for Application No. PCT/US02/37384 dated May 19, 2003.
International Search Report and Written Opinion for Application No. PCT/US2008/079826 dated Apr. 20, 2009.
International Preliminary Search Report for Application No. PCT/US2008/079826 dated Apr. 20, 2010.
International Search Report and Written Opinion for Application No. PCT/US2008/083115 dated Apr. 24, 2009.
International Preliminary Search Report for Application No. PCT/US2008/083115 dated May 18, 2010.
Examiner's First Report on Australian Patent Application No. 2006306361 dated Sep. 6, 2011.
Examination Report for Australian Patent Application No. 2011331936 dated Jun. 24, 2014.
Canadian Office Action for Application No. 2,642,135 dated Mar. 24, 2010.
Canadian Office Action for Application No. 2,642,135; dated Oct. 4, 2011.
Office Action for Chinese Application No. 200680043998.7 dated Jan. 29, 2010.
Translation of Second Notification of Office Action for Chinese Application No. 200680043998.7 dated Jul. 14, 2010.
Office Action for Chinese Application No. 200680043998.7 dated Oct. 27, 2010.
Office Action for Chinese Application No. 201180056406.6 dated Jul. 3, 2014.
Supplementary European Search Report for Application No. EP 02 78 9809 dated May 28, 2009.
Office Action for Application No. EP 02 789 809.7 dated Oct. 22, 2009.
Communication from the Examining Division for EP Application 02 789 809.7, dated Mar. 18, 2010.
Communication for European Application No. EP 02 789 809.7 dated Sep. 21, 2010.
EP Further Observations Under Art. 115 EPC for EP Application No. 02 789 809.7; dated Oct. 15, 2010.
Intention to Grant for EP Application No. 02 789 809.7 dated Apr. 27, 2011.
Supplementary European Search Report for Application No. EP 08 84 0766 dated Apr. 10, 2014.
Office Action for European Application No. EP 08 84 0766.3 dated Apr. 29, 2014.
Extended European search report for EP Application No. 05 85 5170.6, dated Jun. 4, 2010.
Office Action for European Application No. 05 855 170.6 dated Jan. 31, 2011.
Translation of EP1101506 Claims; EuropeanPatentOffice.pdf; Mehner, et al; Jul. 3, 2002; Cited on Form PTO-892 and included with Notice of Allowance issued in U.S. Appl. No. 12/029,159, dated Jun. 28, 2011.
Translation of EP1101506 Description; EuropeanPatentOffice.pdf; Mehner, et al; Jul. 3, 2002; Cited on FOrm PTO-892 and included with Notice of Allowance issued in U.S. Appl. No. 12/029,159, dated Jun. 28, 2011.
Espacenet—INPADOC patent family EP1101506.pdf; included with Notice of Allowance issued in U.S. Appl. No. 12/029,159, dated Jun. 28, 2011.
Office Action for Japanese Application No. 2008-537841 dated Mar. 30, 2012.
Office Action for Japanese Application No. 2008-537841 dated Oct. 2, 2012.
Office Action for Japanese Application No. 2013-541016 dated Jun. 3, 2014.
Office Action for Korean Application No. 10-2008-7012245 dated Jan. 30, 2012.
Office Action for Korean Application No. 10-2008-7012245 dated Sep. 21, 2012.
Office Action for Korean Application No. 10-2013-7016190 dated Jun. 27, 2014.
Office Action for U.S. Appl. No. 11/257,229 dated Apr. 16, 2008.
Office Action for U.S. Appl. No. 11/257,229 dated Sep. 25, 2008.
Office Action for U.S. Appl. No. 11/257,229 dated Mar. 10, 2009.
Office Action for U.S. Appl. No. 11/257,229 dated Sep. 1, 2009.
Notice of Allowance for U.S. Appl. No. 11/257,229 dated Jun. 17, 2010.
Office Action for U.S. Appl. No. 11/315,049; dated Mar. 21, 2012.
Office Action for U.S. Appl. No. 12/742,358 dated Mar. 20, 2012.
Office Action for U.S. Appl. No. 12/742,358 dated Aug. 2, 2012.
Office Action for U.S. Appl. No. 12/845,475 dated Jul. 27, 2011.
Notice of Allowance for U.S. Appl. No. 12/845,475 dated Dec. 23, 2011.
Office Action for U.S. Appl. No. 13/267,434; dated Nov. 8, 2013.
Notice of Allowance for U.S. Appl. No. 13/267,434 dated Feb. 19, 2014.
Office Action for U.S. Appl. No. 13/302,484 dated Dec. 30, 2013.
Office Action for U.S. Appl. No. 13/302,484 dated Jul. 29, 2014.
"Enema Container for X-ray in Large Bowel—Enemaunit," Horri Pharm. Ind., Ltd., dated Oct. 1, 1977.
"Enemaunit—disposable Implement for Intestinal Infusion Upon X-Ray Testing in Large Bowel," Horii Pharm. Ind., Ltd., dated Jul. 1998.
"E-Z-EM Balloon Inflators Cat. No. 9529 [Ref 9529EU];" Merry X-Ray ; Product: 250422; retrieved on Nov. 14, 2013 from <http://orders.merryxray.com/webapp/wcs/stores/servlet/ProductDisplay?-catalogId=11202&storeId=10051&productId=25341&langId=-1&parent_category_rn-=20280&1v10=19579&1v11=19737&1v12=&1v13=>.
"E-Z-EM Flexi-Cuff silicone elastomer retention cuff;" Merry X-Ray—Product: 263980; retrieved on Nov. 14, 2013 <http://orders.merryxray.com/webapp/wcs/stores/servlet/ProductDisplay?- catalogId=11202&storeId=10051&productId=25387&langId=-1&parent_category_rn-=20280&1v10=19579&1v11=19737&1v12=&1v13=>.
"E-Z-EM Flexi-Tip;" Merry X-Ray—Product: 190005; retrieved on Nov. 14, 2013 from <http://orders.merryxray.com/webapp/wcs/stores/servlet/Produ- ctDisplay?catalogId=11202&storeId=10051&productId=25345&langId=-1&parent_category_rn=20280&1v10=19579&1v11-19737&1v12=&1v13=>.
"E-Z-EM hard bulb or E-Z-EM E-Z-Flat device;" Merry X-Ray—Product: 292003; retrieved on Nov. 14, 2013 from <http://orders.merryxray.com/webapp/wcs/stores/ servlet/ProductDisplay?catalogId=11202&storeId=10051&productId=2540 5&langId=-1 &parent_category_rn=101313&1v10=19579&1v11=19737&1v12=&1v13=>.
PROTOC0.sub.2L.TM., Automated Carbon Dioxide Insufflation System for Virtual Colonoscopy; E-Z-EM; Virtual Colonoscopy; retrieved on Dec. 9, 2005 from <http://www.ezem.com/virtual_colon/proto.htm>.
Extended European Search Report corresponding to EP Application No. 14188116.9 dated Feb. 17, 2015.
Office Action for Canadian Application No. 2,702,489 dated Jun. 1, 2015.
Office Action for Mexican Application No. MX/a/2013/005850 dated Jun. 25, 2015.

(56) References Cited

OTHER PUBLICATIONS

Office Action dated Aug. 13, 2015 in corresponding U.S. Appl. No. 13/402,455.
Notice of Allowance dated Jul. 14, 2015 in Canadian Application No. 2,818,844.
Notice of Allowance dated Sep. 1, 2015 in Japanese Application No. 2013-541016.
Official Action dated Oct. 14, 2015 in EP Application No. 11 790 835.0.
Notice of Allowance for U.S. Appl. No. 13/302,484 dated Sep. 19, 2016.
Office Action dated Jan. 20, 2016 in U.S. Appl. No. 13/402,455.
Official Action dated Oct. 21, 2015 in U.S. Appl. No. 13/302,484.
Notice of Acceptance dated Feb. 19, 2015 in Australian Application No. 2011331936.
Office Action in Chinese Application No. 201180056406.6 dated Jan. 23, 2015.
Office Action in Japanese Application No. 2013-541016 dated Feb. 10, 2015.
Office Action in Korean Application No. 10-2013-7016190 dated Dec. 29, 2014.
Office Action dated Jan. 29, 2015 regarding U.S. Appl. No. 13/402,455.
Office Action dated Jan. 20, 2015 regarding U.S. Appl. No. 13/711,802.
Office Action dated Apr. 9, 2015 regarding U.S. Appl. No. 13/302,484.
Extended European Search Report dated Feb. 17, 2015 regarding European Application No. 14188116.9.
Office Action dated Apr. 17, 2017 in U.S. Appl. No. 14/273,066.
Examination Report for European Patent Application No. 14188116.9 dated Aug. 23, 2019.
Epuropean Published Application No. EP 28482192 dated Mar. 18, 2015 and claim amendments made after the publication.

\* cited by examiner

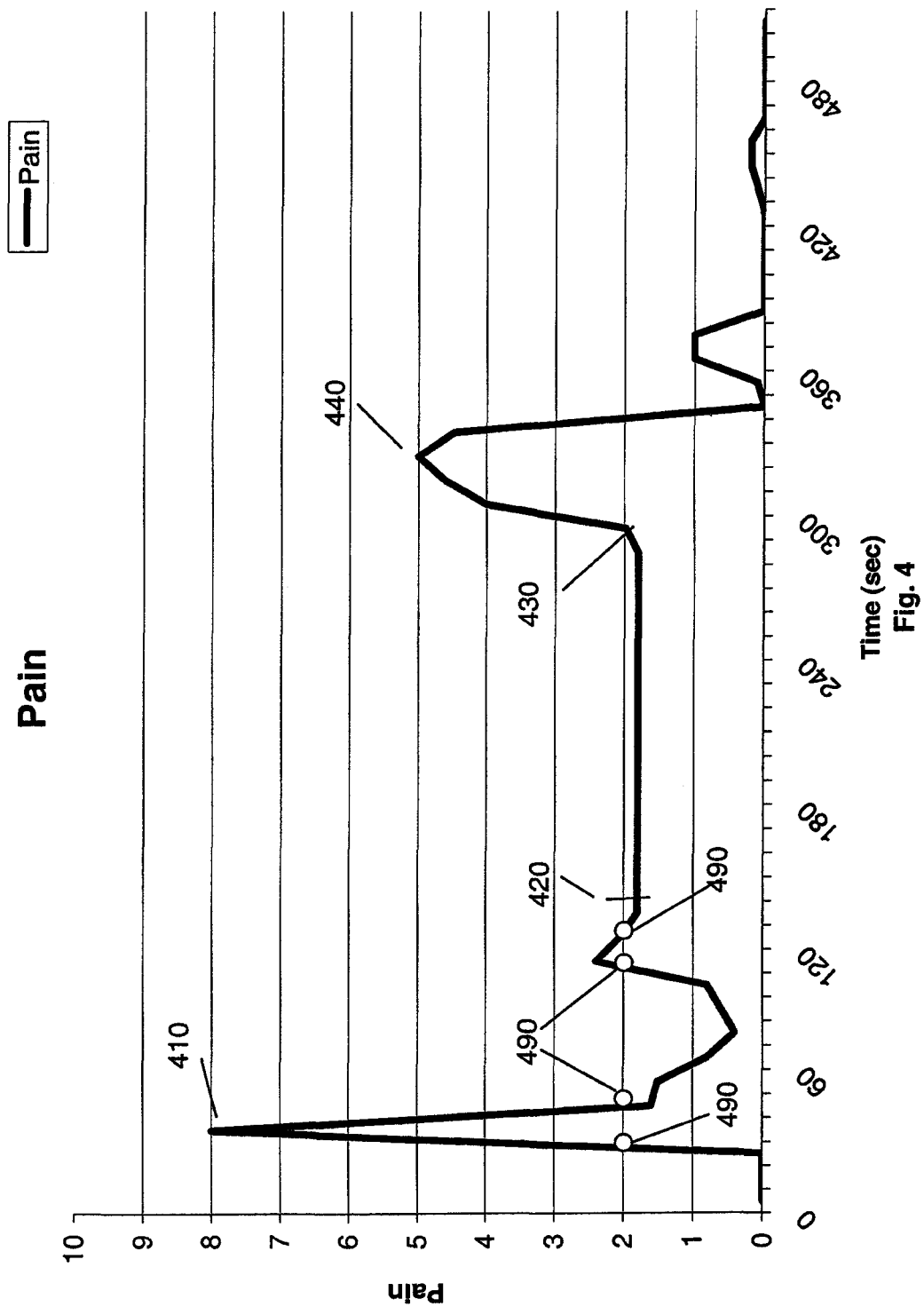

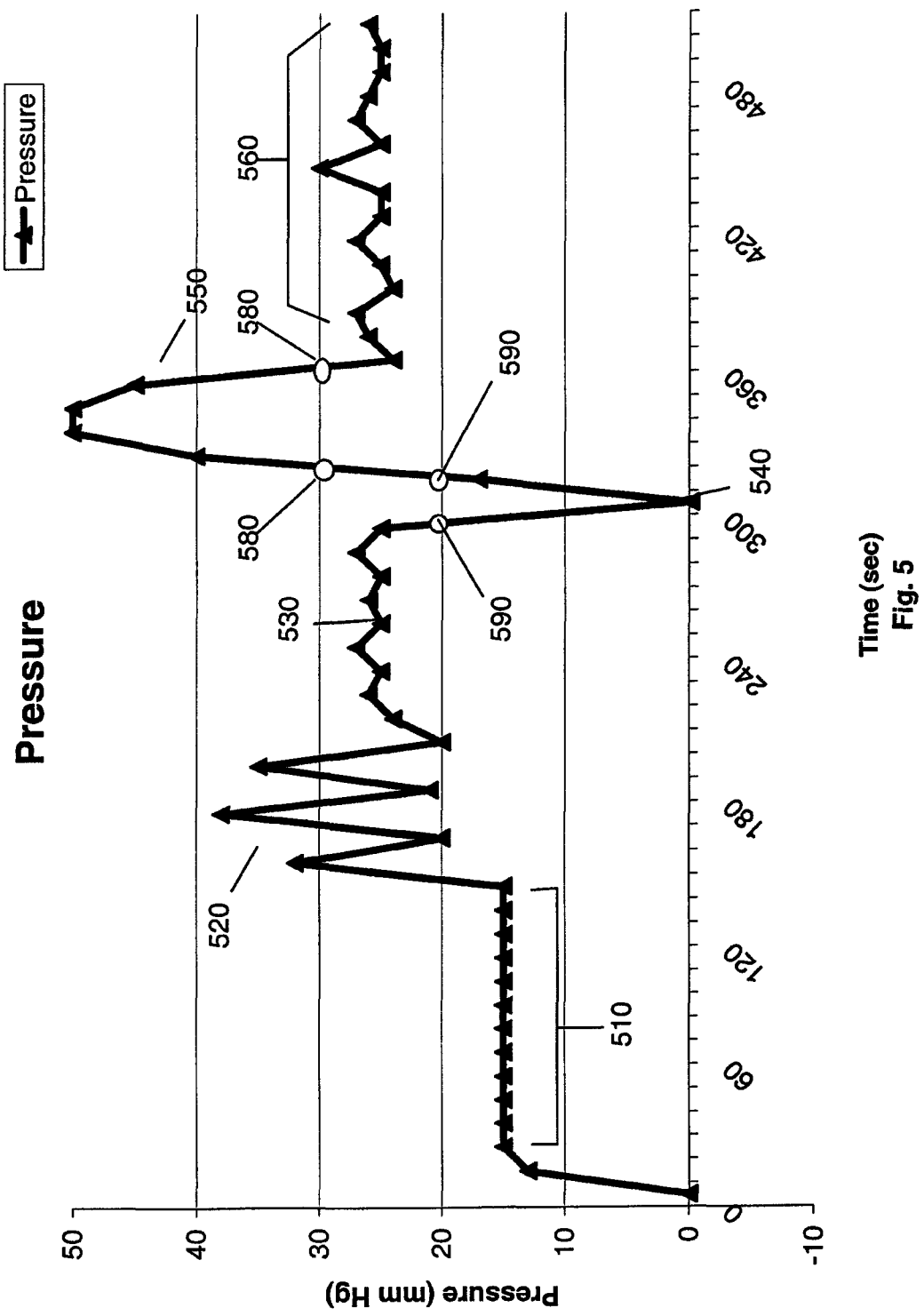

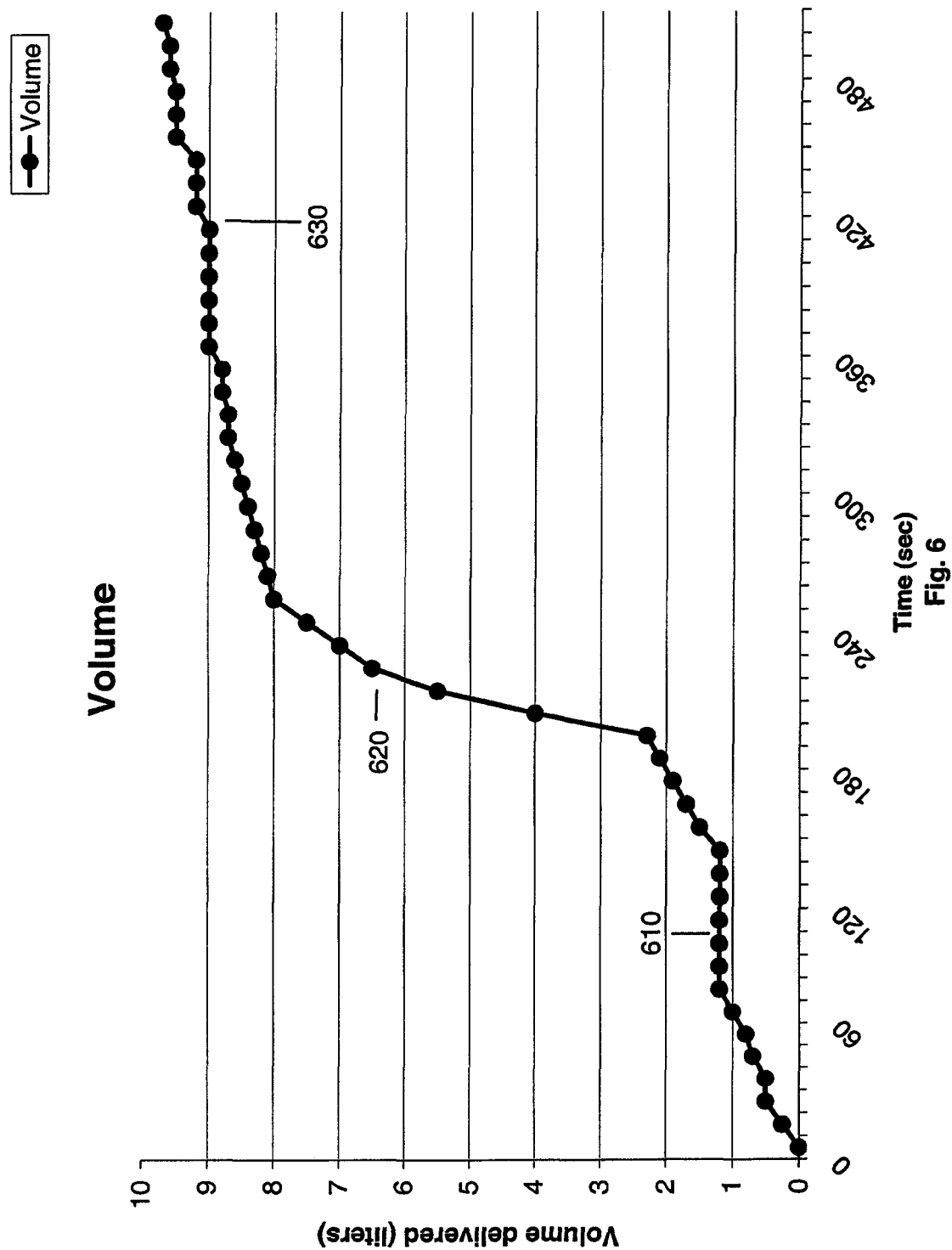

APPARATUS AND METHOD FOR USE IN ANALYZING A PATIENT'S BOWEL

PRIORITY CLAIM

This application is a continuation of U.S. patent application Ser. No. 14/459,365, filed Aug. 14, 2014, which is a continuation of U.S. patent application Ser. No. 12/682,963, filed Apr. 14, 2010, which is a National Stage Application of International Application No. PCT/US2008/079826, filed Oct. 14, 2008, which claims priority to U.S. Provisional Patent Application No. 60/979,962, filed Oct. 15, 2007, the entire disclosures of which are hereby incorporated by reference.

FIELD OF THE INVENTION

The present invention relates to an apparatus and method for use in analyzing a patient's bowel by indicating selected parameters, such as colonic pressure, and perceived patient sensations, such as pain, during a medical procedure such as a virtual colonoscopy examination, or for use as a diagnostic testing means.

BACKGROUND OF THE INVENTION

Virtual colonoscopy (VC) is an effective medical procedure for use in identifying polyps and cancers in the bowel. Typically, an oral laxative is administered to a patient to cleanse and empty the bowel of solid stool. Once the bowel is cleansed, the colon is insufflated with gas. After the colon is distended by the gas, the patient's abdomen and pelvis are scanned using a selected scan procedure, such as computed tomography (CT) or magnetic resonance imaging (MRI), while the patient lies motionless during a breath hold. Finally, image analysis is performed by a physician and/or computer-aided diagnosis to diagnose polyps, cancer or other abnormalities in the bowel.

Colonic insufflation usually involves administering air or other selected gas into a patient's colon through a rectal catheter. A technologist monitors the flow of gas through the rectal catheter into the colon. Once the technologist believes that the colon has been sufficiently insufflated the patient's abdomen and pelvis are scanned.

Subjective determination of colon distention during a VC procedure has several drawbacks. For example, false readings may be obtained if the colon is not properly distended throughout the CT or MM scan. An improperly distended colon, or a colon affected by contractions (including normal peristalsis and spasms) may produce misleading images and errors in diagnosis because of the potential of collapsed bowel segments mimicking or masking true lesions. Furthermore, patient intolerance to colonic distention can lead to patient motion, either respiratory or body movements, during the scan which can also produce image artifacts that lead to incorrect diagnoses.

Accordingly, an apparatus for objectively determining distention of the colon and relative patient sensations, hence improving the accuracy of a medical procedure such as a VC scan, and for use as a diagnostic test, is desirable.

SUMMARY OF THE INVENTION

In accordance with the present invention, an apparatus and method are provided for use in analyzing a patient's alimentary tract, and, more particularly, for use during a scan of a patient's colon. In accordance with the present invention, a sensory input detector is provided. The sensory input detector may be in the form of a pain input detector that communicates with the patient for detecting pain perceived by the patient during insufflation of the patient's colon with gas. The pain input detector may optionally include a pain sensor such as a squeeze bulb which may be squeezed by the patient to indicate the onset of pain and may be released by the patient to indicate the cessation of pain. The magnitude of squeeze on the squeeze bulb can also be determined based on pressure changes caused by squeezing and releasing of the bulb to correlate to a magnitude of pain perceived by the individual patient.

The apparatus may also include a sensory transducer, for example, as a part of the sensory input detector to provide at least one parameter indicative of a parameter such as pain perceived by the patient. More specifically, the sensory transducer may produce an output parameter to indicate the onset or cessation of pain. Optionally, the pain transducer may be used to produce an output parameter to indicate sensations perceived by the patient, such as a magnitude of perceived pain. In other arrangements the sensory transducer may function to produce an output parameter to indicate other sensations the patient may perceive by any of the senses, including but not limited to, touch, sight, hearing, taste, or smell.

A processor may be provided for communicating with the sensory transducer to generate an output reflecting perceived patient pain. The output may, alternatively, indicate other physiological parameters or sensory parameters. Sensory parameters include sensations perceived by the patient, whereas physiologic parameters include indications concerning the status of insufflation of the patient's colon. The output may then be used to determine validity or invalidity of a scan of a patient. For example, if the output is within a selected threshold, the scan may be determined to be valid. Optionally, if the parameter is outside of a selected threshold, the output may be used to indicate that a scan is not valid. A determination of validity may be conducted before the scan is performed. For instance, the output may be used to determine whether one or more parameters are within a selected threshold. If the one or more parameters have obtained the selected threshold, the scan may be conducted and reliable results may be obtained. If selected parameters are not within the selected threshold, reliable scan results may not necessarily be obtained. For instance, if selected parameters indicate that the patient's bowel is not insufflated to a desired amount, any scan that might be performed may not yield accurate results. Validity determinations conducted before a scan may be referred to as "approval." Optionally, validity may be determined during the patient scan. During the patient scan, if one or more parameters are within a selected threshold, the scan results may be accurate, thereby providing a valid scan. Alternatively, if the parameters are not within a selected threshold, the scan may be considered invalid and the patient may be scanned again. For example, a scan may be determined to be invalid if bowel segments are found to be collapsed during the scan. Validity determinations conducted during a scan may be referred to as "verification." In short, validity may be determined before a scan (approval) or validity may be determined during a scan (verification).

Signaling means may be provided to signal the technologist or physician when the output reflects the predetermined condition to validate a selected medical procedure such as a VC scan. Various medical procedures require the patient to be scanned. Examples include VC scans, CT scans, MRI scans, or any other similar procedures. Specifically, the term "VC scan" used herein includes both CT and MRI scans of a patient's colon. An indication that a VC scan is invalid may be used to prevent the commencement of a CT or MM scan or may be used to indicate that an ongoing or already completed scan may need to be repeated.

In an alternate embodiment, the apparatus may include a gas pressure transducer that may be used either alone or in combination with the sensory input detector, such as a pain input detector, to provide a physiologic parameter, such as a parameter of gas pressure within the patient's colon or alternatively, pain perceived by the patient. The gas pressure transducer communicates with the patient's colon for indicating gas pressure inside the lumen of the patient's colon. The processor may be utilized in communication with the gas pressure transducer to generate an output parameter reflecting the pressure of the gas in the patient's colon. A signaling means may be provided to signal when at least one selected output parameter reflects a predetermined condition to validate a procedure such as a VC scan of the patient. More specifically, the signaling means may be used to signal when an output from the gas pressure transducer and/or the pain transducer is outside of a selected threshold(s) thereby indicating an invalid scan. Likewise, the signaling means may be used to signal when the selected output parameter, such as pressure within the colon and/or pain perceived by the patient, is within a selected threshold(s) to indicate that a scan of the patient is valid.

In accordance with another embodiment of the invention, a flow meter may be used to measure flow of gas being instilled into the colon of the patient. The flow meter in a selected embodiment may be used alone or in combination with either the gas pressure transducer or the sensory input detector, or both of them, to detect multiple or additional physiologic or sensory parameters. In such an embodiment utilizing a flow meter, the processor communicates with the flow meter to generate an output parameter reflecting the volume of gas delivered to the patient. Again, the signaling means may be used to signal when at least one output parameter, such as the volume of gas delivered to the patient, reflects a predetermined condition to validate the scan of the patient. More specifically, the signaling means may be used to signal when the selected output parameter, such as volume of gas delivered to the patient, is within a selected threshold to validate the scan or when the parameter is outside of a predetermined threshold to indicate an invalid scan. In accordance with one embodiment, the processor may take the form of a conventional microprocessor and assorted circuitry, a data acquisition module (DAQ), other hardwired circuitry, software, or much more simplified circuitry, such as an amplifier, converter, memory or display circuitry.

In another embodiment, a method is provided for use in studying a patient's colon during a selected scan procedure by generating an output reflecting a selected parameter such as a parameter relating to perceived patient pain during the scan. The method may be used when a patient's colon is insufflated during a medical procedure such as a VC scan or it may be used as part of a diagnostic test. In a particular application, the patient's colon is insufflated with gas. At least one parameter indicative of a sensation, such as pain, perceived by the patient during or after colon insufflation is detected. Then a determination is made whether the at least one parameter is within a threshold. For example, the validity of a medical procedure, such as a VC scan, may be determined if the parameter is within the threshold. Alternatively, a diagnostic test for disease may be performed based upon a determination of whether the parameter is within or outside a selected threshold.

BRIEF DESCRIPTION OF THE DRAWINGS

The foregoing summary as well as the following description will be better understood when read in conjunction with the figures in which:

FIG. 4 is an exemplary chart of a hypothetical representation of a selected parameter of perceived patient pain in accordance with the present invention.

FIG. 5 is an exemplary chart of a hypothetical representation of a selected parameter of colonic pressure in accordance with the present invention.

FIG. 6 is an exemplary chart of a hypothetical representation of a selected parameter of volume of gas delivered to a patient in accordance with the present invention.

DETAILED DESCRIPTION OF THE INVENTION

Referring now to the Figures in general, wherein like reference numbers refer to the same components across the several views, there is shown an apparatus, generally designated 100, for use in a selected medical procedure or diagnostic test. In general application, the apparatus 100 may be used as a monitoring apparatus to monitor selected conditions of a patient during the selected medical procedure or diagnostic test. In specific application, the apparatus 100 may be utilized to monitor selected physiological and/or sensory parameters of a patient during a medical procedure, for example, during a scan of the patient's abdomen and colon or other type of body scan. The term "VC scan" as used herein encompasses both CT and MRI scans. In order to scan a patient's colon, the patient must be properly prepped for the scan. First, the patient's colon must be cleansed. Immediately prior to the VC scan, the patient's colon is insufflated with gas to distend the colon so that a clear image may be obtained during the scan procedure. Gas from an insufflator 24 is administered to the patient to distend the patient's colon. Although air has traditionally been used to insufflate the colon, the gas insufflator 24 may employ carbon dioxide, nitric oxide, xenon, krypton, oxygen, or other gas. In one preferred embodiment, carbon dioxide is dispensed from the insufflator 24 into the patient. The flow rate of gas delivered may be at a preset rate or amount. For instance, the rate of gas flow delivered to the patient may be approximately 3 to 5 liters per minute. In another configuration, an insufflator which is capable of delivering a higher flow rate may be used. For instance, a gas insufflator capable of delivering 20 to 30 liters per minute may be used in various procedures. In order to aid in producing a valid scan of the patient's colon, the apparatus 100 may be used to monitor selected physiological and sensory parameters of the patient, such as pressure inside the colonic lumen, gas flow into the colon, volume of gas delivered to the colon, and/or pain or other sensations perceived by the patient during the insufflation procedure. Other conditions of the patient may also be monitored for specific applications.

Figure 1:
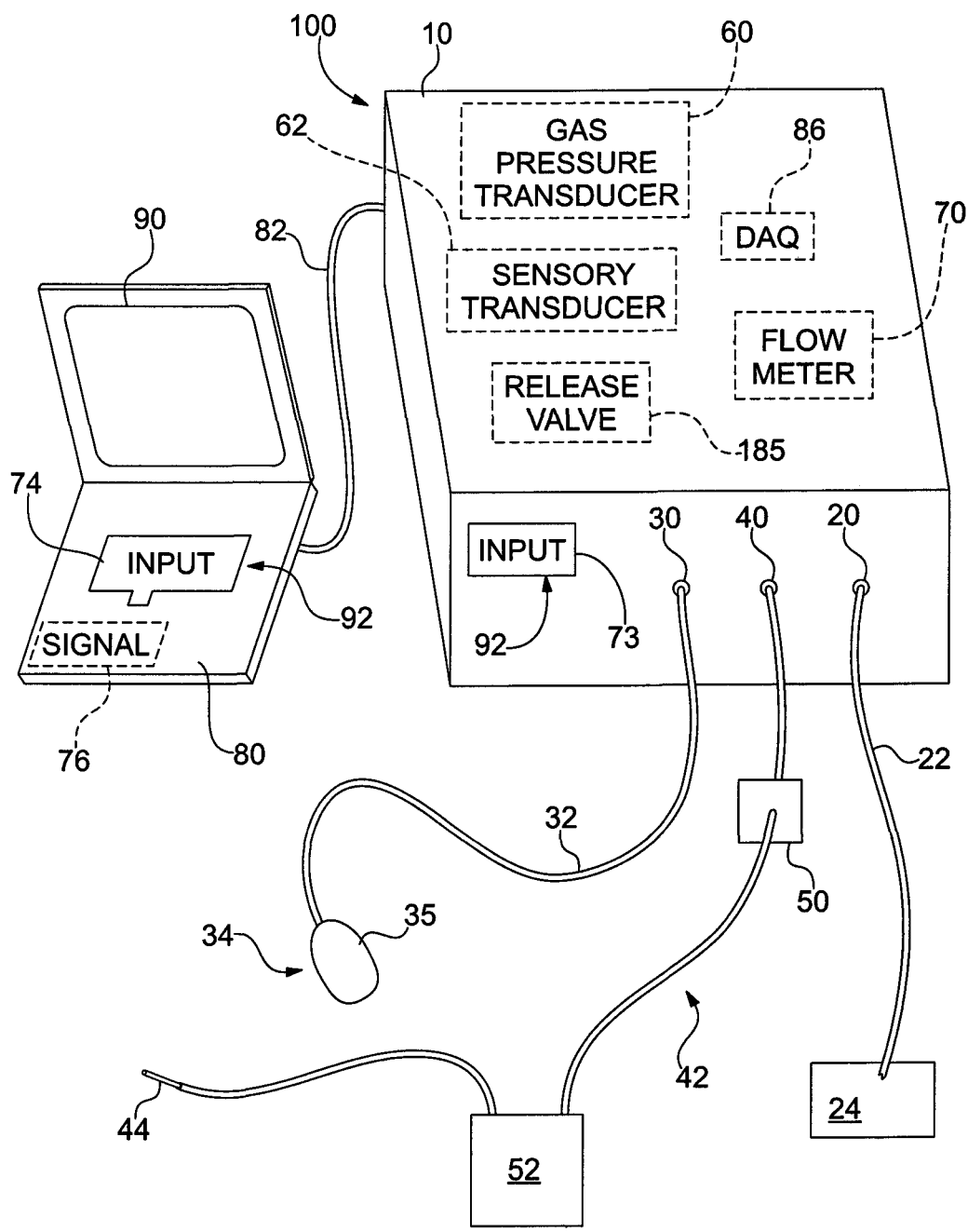
FIG. 1 is a schematic perspective view of a monitoring device in accordance with the present invention.
Figure 2:
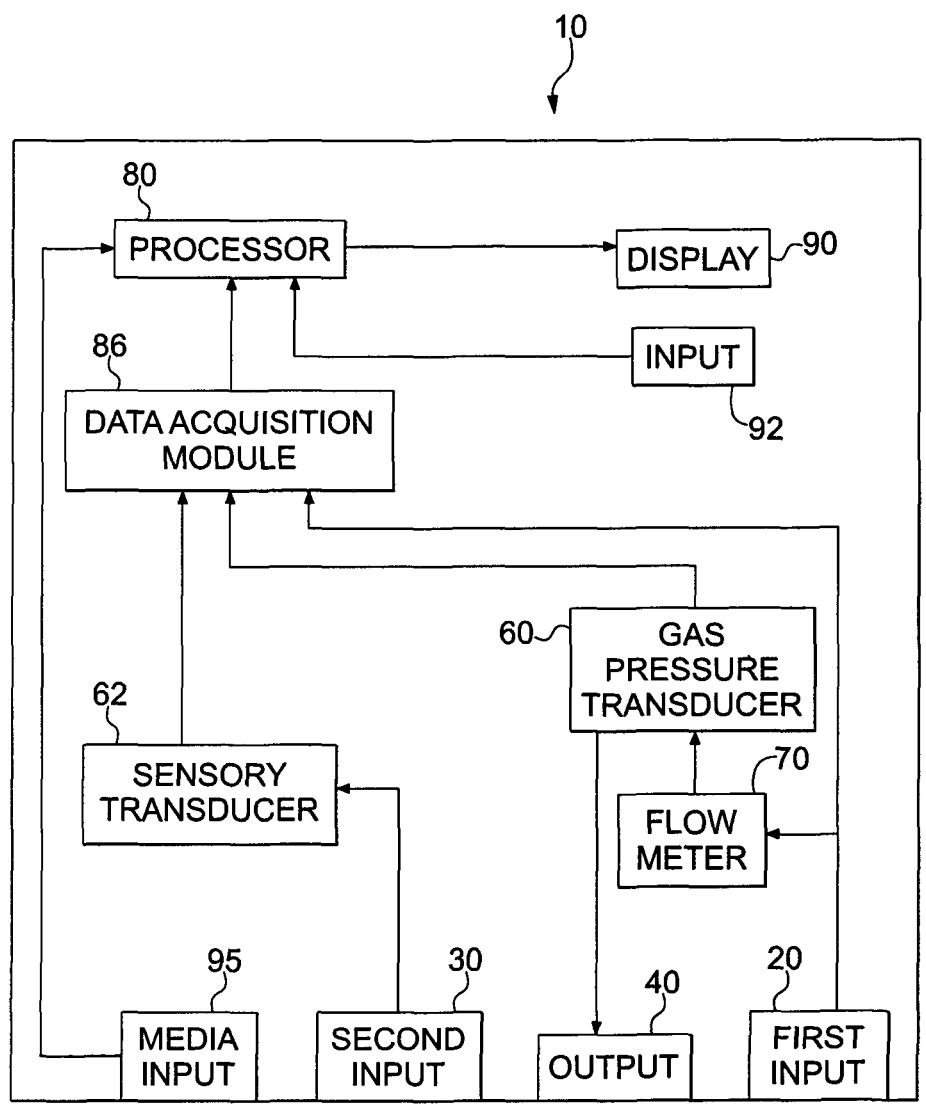
FIG. 2 is schematic diagram of one configuration of a monitoring device in accordance with the present invention.

As shown in FIG. 1, the apparatus 100 includes a housing 10. In order to measure the flow of gas supplied to the patient's colon, the apparatus 100 includes a gas flow meter 70. In order to supply gas to the patient's colon, a gas insufflator 24, is connected with a first input 20 on the apparatus 100 by a supply tube or input line 22. A gas tank provides gas to the insufflator 24 for insufflation to the patient. From the input 20, the gas flow is directed through the flow meter 70 so that the flow of gas from the gas insufflator can be measured in selected units such as liters per second. From the gas flow meter 70, the gas flow is directed out of the apparatus 100 through output 40 and is supplied through output tube or line 42 to the patient's colon through a rectal catheter 44 that is inserted into the patient's rectum. A waste collector 52, such as a canister or plastic bag, is provided between the rectal catheter 44 and the output 40 of the apparatus 100 to collect any undesirable back flow of waste from the rectal catheter. In order to decrease the risk of contamination of the apparatus 100, a hydrophobic filter 50 is positioned between the waste collector 52 and the output 40 to impede back flow toward the apparatus 100. In this arrangement, the gas flow meter 70 is positioned within the flow of gas from the gas insufflator 24 to the rectal catheter 44. The gas flow meter 70 is used to produce an output flow parameter reflecting the amount or rate of flow of gas delivered to the patient's colon. The output flow parameter may be processed internally of the unit 100 by processor circuitry to generate, if desired, an output reflecting the rate of gas delivered to the patient and/or the volume of gas delivered to the patient. The processor circuitry may include a conventional processor 80, a microprocessor and assorted circuitry, a data acquisition module (DAQ) 86, other hardwired circuitry, or software, or much more simplified circuitry such as an amplifier, converter, memory or display circuitry and/or software. The processor 80 may be positioned inside the housing 10 or may be positioned external from the housing 10. The flow of gas over time may be measured to produce an output volume parameter providing an indication of the volume of gas delivered.

In order to detect or measure the pressure of gas within the patient's colon, a gas pressure transducer 60 is provided in the apparatus 100. The gas pressure transducer 60 communicates with the patient's colon for detecting gas pressure within the patient's colon. For example, the gas pressure transducer 60 may communicate at a selected point along the output line 42, the input line 22, or at a position within the apparatus 100 between input 20 and output 40. A separate gas detection line could be run with or through the rectal catheter directly into the patient if so desired. In a selected application, for example, the gas pressure transducer may be connected along the flow line at a location before the hydrophobic filter 50. The gas pressure transducer 60 functions to produce an output pressure parameter reflecting the gas pressure within the patient's colon. The output parameter from the gas pressure transducer may be processed by the data acquisition unit 86 and/or by the processor 80 to produce an output, if desired, reflecting the gas pressure within the colon.

In order to measure pain sensation perceived by the patient, a sensory transducer 62, in the form of a pain transducer, is provided on the apparatus 100. "Pain" as used herein includes pain and/or discomfort perceived by the patient. In this particular configuration, the sensory transducer 62 functions as a pain transducer to monitor pain perceived by a patient and to produce an output pain parameter reflective of the perceived pain. Otherwise, the output generated by the sensory transducer 62 may include data reflecting other physiological and sensory parameters. Sensory parameters include sensations perceived by the patient including, but not limited to, touch, hearing, sight, smell, and taste. For example, the patient may feel sensations such as temperature, visceral pain, pressure, or tenesmus. Accordingly, while the sensory transducer 62 may measure pain, the sensory transducer 62 may be configured to also measure other sensory parameters perceived by the patient. The sensory transducer 62 communicates with an input sensor 35, with which the patient communicates. In this particular configuration, the sensory transducer 62 functions as a pain transducer that communicates with a pain input detector 34 through input line 32 connected between the sensory input detector 34 and an input 30 on the apparatus 100. The sensory input detector 34, when in the form of a pain input detector 34, communicates with the patient in order to detect pain perceived by the patient. For this purpose, the input sensor 35 may include a sensor in the form of a squeeze bulb 35 that may be actuated by the patient in response to perceived pain or other sensations. For example, the squeezing of the bulb 35 will serve to change the pressure within the bulb so as to indicate the onset of pain. Likewise, the release of the bulb 35 will change the pressure within the bulb in the opposite direction to thereby indicate the cessation or reduction of pain perceived by the patient. The amount the bulb 35 is squeezed or released can be detected to determine a change in magnitude, either up or down, in the amount of perceived pain. Similarly, the length of time that the bulb 35 is squeezed and then released can be measured to determine the duration of pain as well as the duration of different magnitudes of pain perceived by the patient. In such an arrangement, the pain transducer 62 may take the form of a pressure transducer so as to detect changes in pressure created at the squeeze bulb 35 by the patient in response to pain. In such an arrangement, the pain transducer 62 will output a pain parameter reflective of perceived pain. The output pain parameter may be used to indicate absence of pain, onset of pain, reduction of pain, cessation of pain, increase of pain, change in pain, magnitude of pain, as well as duration of pain and duration of selected magnitudes of pain. The output parameter from the pain transducer 62 may be supplied to the DAQ 86 and/or the processor 80 in order to process the data to generate an output, if desired, reflecting perceived pain or a parameter of the perceived pain. Of course, more generally, the change in pressure may also be measured up or down, and timed by the sensory transducer 62 in the form of a general pressure transducer to reflect other sensations or parameters.

The DAQ 86 may function as a type of processor in certain applications or configurations to control and generate output data in desired format for selected uses such as further processing, display, analysis, or storage. The DAQ 86 may be used to communicate with any one or a combination of the gas pressure transducer 60, the sensory transducer 62 and the flow meter 70, or other selected inputs. The data reflecting the output parameters from the gas pressure transducer 60, the sensory transducer 62 and/or the flow meter 70 may be communicated via the DAQ 86 to the external processor 80 for original or further processing. A selected output reflecting at least one of the output parameters, including any one alone or in combination with the others, may be generated and displayed on a display 90. An input 92 to enable a user to input information or data may be provided on the apparatus 100, such as input 73, or on the computer processor 80, such as input 74, or on both the apparatus 100 and the computer processor 80. The components of the apparatus 100 may also be positioned within one housing 10. Preset limits or other programmed information may be entered into the input 92. If desired, the processor 80, the display 90, and the input 74 may be incorporated within the monitoring apparatus 100 as an integral device.

Signaling means or unit 76 may also be provided to indicate at least one parameter reflective of a predetermined condition so as to determine the validity of a medical procedure such as a VC scan. Generally, the signaling means 76 may be positioned for use with the apparatus 100 or the external processor 80. The signaling unit 76 may be provided to indicate that favorable conditions exist in order to start the scan of a patient or that favorable conditions have occurred during the performance of a scan, hence indicating a valid scan. A determination of validity conducted before the start of a scan may be referred to as "approval." A technologist or doctor may determine whether one or more parameters have obtained a selected threshold. If the parameters fall within the selected threshold, the results may be deemed valid and approval given that a scan may be started. If the parameters are not within a selected threshold, approval may not be given so that the results may be considered invalid and a scan may not be conducted. An exemplary situation where a procedure would be considered invalid could occur if parameters do not reach a selected threshold because the patient's colon is not distended. A determination of validity made during a scan may be referred to as "verification." If one or more parameters are within a selected threshold as the patient is being scanned, the technologist or physician may determine the scan is valid and verify the scan results. However, if the parameters are not within the selected threshold, the technologist or physician may not verify the parameters and instead declare the scan to be invalid. An example of a situation where a scan may be deemed invalid would occur if a section of bowel collapses during the scan. Alternatively, determination of validity may incorporate an automated process such as computer-aided diagnosis (CAD). For instance, the signaling unit 76 may indicate whether an unfavorable condition occurred during the course of a scan, thereby indicating an invalid scan or an invalid segment of a scan. For this purpose, the signaling unit 76 may take a variety of different formats and may be in the form of an electronic signal, an alarm, a flashing light, sound alarm, or other suitable signaling means in desired hardware and/or software.

Representations of the output parameters indicating gas pressure, gas volume, and pain, for example, may be displayed on the display 90. The representations may be displayed as functions or other wave forms on the display, or the representation may take the form of text or verbal messages. In selected applications, the output parameters may be displayed in strip chart format on the display 90. Alternatively, one or more output parameters could be displayed as bars or other types of graphs or charts. The display 90 may function to display one or more parameters at the same time, for example, superimposed on one another as shown for example in FIG. 3 or in separate display sections as shown for example in FIGS. 4, 5, and 6. The display 90 may also be caused by the processor to display the representations separately. The data shown on a display 90 may be analyzed, whether or not the data is actively displayed, by a technologist, physician, or CAD to determine if the pressure in the colon, the volume of gas delivered to the patient, and/or the amount of pain or discomfort experienced by the patient as the patient's colon is insufflated meets a selected threshold or criteria. Other sensations perceived by the patient and detected by the sensory input detector 34 may also be shown on the display 90. The processor 80 may analyze physiological and sensory parameters to diagnose certain conditions of the patient.

The output generated by the processor 80 to reflect at least one output parameter may be used by the technologist, physician, or CAD to make decisions concerning patient care or to confirm (i.e., approve or verify) a clinical procedure. A determination may be made as to the validity of a scan of the patient. Validation is effected to determine when to start a scan, whether to stop a scan already in progress or whether a scan or any part thereof may need to be repeated under more favorable conditions. Typically, for relatively short scans, the scan would not be stopped but may need to be repeated to acquire image data under more favorable conditions. For a relatively lengthy scan, it may be desirable to stop the scan, for example, in order to prevent unnecessary radiation exposure whenever CT is being employed as the scanning method. Additionally, a determination may be made as to efficacy of pharmacological intervention after such intervention has been administered. For example, the output data may be analyzed to determine a decrease in patient pain perception or colonic pressure spikes when a pharmacological agent, such as a spasmolytic agent, is administered. In one exemplary embodiment, for example, plotted data representing the gas pressure within the colon may resemble a plateau-like shape at a desired level when the has reached a steady state suitable for scanning. The plateau-like shape indicates that gas pressure is steady and the bowel is relaxed. A steady state of gas pressure within the colon at a suitable level may provide the greatest amount of colonic distention and the least amount of patient discomfort. Once a steady state has been reached, the patient may be scanned. By performing the scan when the bowel is relaxed, the accuracy of the scan results increases, thereby reducing the likelihood of the physician making erroneous diagnoses caused by bowel contractions that can mimic or mask cancers or other abnormalities. By providing more accurate determination of colon distention, the likelihood of having to repeat a VC scan due to poor readings is decreased, thereby reducing or eliminating unnecessary additional time, cost, and when CT is employed as the imaging means, radiation exposure.

During a procedure, data processed by the processor 80 may instead indicate the presence of contractions in the colon. Peristalsis is the normal contraction of the bowel that propagates contents along its lumen, whereas spasm is an exaggerated form of contractions that is often perceived by the patient as cramping. The term "contraction" as used herein refers to both peristalsis and to spasm. Contractions of any form may cause normal areas of the colon wall to appear on scan images as abnormally thickened or collapsed. Accordingly, contractions may mimic the presence of an abnormality when in fact none is present. Conversely, the presence of contractions or collapsed segments of bowel during a scan may mask the presence of cancer or polyps. If a scan is performed while the colon contracts or is collapsed, the scan may produce inaccurate results. Therefore, the detection of contractions may call into question the validity of a scan. In such a case, the patient may need to undergo a repeat scan. Accordingly, the output parameters generated may be analyzed to determine the validity of scan results. In general, the output parameters may be analyzed by the technologist, physician, or CAD to determine if any or all of the output parameters fall within a selected threshold to determine the validity of the scan. Conversely, if any or all of the output parameters fall outside a selected threshold the scan may be determined to be invalid.

Considering one exemplary application, the processor 80 may process data for three selected parameters. Specifically, the processor 80 may process an output pain parameter reflecting perceived patient pain, an output volume parameter reflecting volume of gas delivered to the patient, and an output pressure parameter reflecting colonic pressure. Turning now to the pain parameter, the pain input detector 34 indicates perceived patient discomfort, pain, or other sensations. Information reflecting perceived patient pain is detected by an input sensor 35 in communication with the patient. In a selected configuration, the input sensor 35 may include a hand-held squeeze bulb 35, such as a hollow plastic or rubber ball. The bulb 35 is connected by a length of tubing or line 32 to input 30 and is connected with the sensory transducer 62 which may function as a pain transducer. The squeeze bulb detects perceived patient pain and conveys data to the pain transducer 62. For instance, the onset of discomfort may be detected by pain input detector 34 when the patient squeezes the bulb 35. The pain input detector 34 may also detect pain relief as the patient releases the squeeze of the bulb 35. Duration of discomfort may be measured as the length of time between the start of a squeeze and the release of the squeeze. Severity of pain may also be measured by the pain input detector 34. Severity may be indicated by how forcefully the patient squeezes or releases the bulb 35. Specifically, a strong squeeze of the bulb 35, by the patient could indicate a high level of pain. Alternatively, a slight squeeze may indicate a low level of pain or discomfort. Likewise, a quick release may indicate a sudden drop in pain and a slow release may represent a slow drop in pain. Likewise, a partial release may indicate a drop in pain but to a lower level. As the patient squeezes and releases the bulb the changes in pressure produced by the bulb can be tracked both in direction and in magnitude by the sensory transducer 62 which functions as a pressure transducer and part of the pain input detector 34.

In an alternate embodiment, the input detector 34 may be in the form of some other hand-held device with strain transducers to deliver electromechanical input to the sensory transducer 62, or it may take the form of a foot activated pedal or other body activated device, or a voice-activated or other sensory-activated sensor.

Since in the present configuration the pain input detector 34 detects a painful sensation perceived by the patient, it is preferable for the pain sensor 35 to reset rapidly in preparation for another perceived pain event. For instance, if a hand-held bulb is used, the pain transducer 62 detects air pressure at the bulb. The hand-held bulb is made of a resilient material, such as rubber or plastic, so that once a patient releases the sensor, the sensor quickly resets to be able to register another pain indication shortly after release. For this purpose, the resetting of the pain input detector 34 may be controlled by a pressure release mechanism or other similar mechanism. Such optional arrangements may be used to sense or detect parameters other than pain.

In operation, patient pain may be detected on a relative scale which differs for each patient. In one configuration, a range of 0 to 10 may be provided for a patient, where 0 indicates no pain and 10 indicates of pain. A relative pain scale is established by calibrating the pain input detector 34 before starting the procedure. For instance, if the pain input detector 34 utilizes a squeeze bulb, the patient may be asked to squeeze the bulb as hard as possible in order to establish an upper limit of a selected patient's perceived pain. This reading may be established as a "10" on the scale. Calibration of the pain input detector 34 standardizes the patient pain data despite the varying pain threshold of each patient.

Additionally, during the scan procedure the patient may experience a pain sensation that causes him or her to record a pain level that exceeds the calibrated upper limit, or the patient may just happen to squeeze harder during the scan procedure than during the calibration procedure.

Generally, it is desired to acquire a scan as the patient lies motionless and during a breath hold. Excessive pain may cause the patient to breath, squirm or move during the scan which can produce respiratory and/or motion artifacts that can yield inaccurate scan results. If a patient perceives a great deal of pain during colon insufflation, a scan should not be conducted and some form of intervention may be required to relieve the patient's pain. One form of intervention consists of releasing, or venting, gas from the patient's colon. Venting of gas may be conducted either manually by a technologist or it may be automated. For example, the technologist may manually disconnect the tubing 22 from the insufflator 24 so that the colon may be vented to atmospheric pressure. Alternatively, this venting mechanism could be automated and controlled via a pressure release valve 185 mechanism incorporated into the apparatus 100. Intervention could also take the form of pharmacological intervention, such as administration of a spasmolytic agent. On the other hand, if a patient experiences a great deal of pain, but the pain resolves quickly, then no intervention may be required. For example, FIG. 4, number 410 shows a pain spike to level 8 of pain. The pain spike at level 8 may indicate that a high magnitude of pain is perceived by the patient. Since pain spike 410 resolves relatively quickly, intervention may not be required. On the other hand, a pain spike to level 10 may require intervention regardless of how short the duration of the pain. Alternatively, if a patient experiences pain for a sustained length of time, for example, longer than 5 seconds, intervention in the form of venting and/or pharmacologic intervention may be required to reduce pressure and relieve pain before continuing with the insufflation and/or scanning procedure. FIG. 4, number 440 shows sustained pain at level 5 which lasts more than 20 seconds or so and may therefore be longer than a selected time threshold. The selected time threshold may be 5 seconds or some other suitable length of time. The patient may need intervention to decrease colonic pressure and pain. The patient should not perceive any significant pain prior to restarting the insufflation procedure if restarting insufflation is deemed necessary.

In a selected application, a patient may experience mild pain or discomfort but still be scanned. If the patient experiences pain that does not reach a selected threshold, such as a level 2 for example, then a scan may be conducted. For example, a scan may be performed while the amount of pain is below a selected threshold and the patient is relatively pain-free or experiencing only minor discomfort, such as a bloating sensation or tenesmus. In FIG. 4, a valid scan may be conducted between points 420 and 430. For example, if the pain threshold was set at level 2, and the patient perceives pain reflecting a value just under the threshold such as between points 420 and 430, the scan may still be performed. Such data may indicate that the patient's colon is sufficiently distended so that a scan may indicate accurate results. In one situation, such pain data may be combined with data indicating that at least a minimum amount of gas that has been delivered to the patient to indicate accurate results. A scan may be conducted while the patient experiences minor discomfort between points 420 and 430, but not while the patient experiences sudden sharp pain 410. Even though intervention may not be necessary at point 410, the scan may still be invalid if a threshold of level 7, for example, was selected.

Colonic pressure inside the colon lumen is another variable which may be processed by the processor 80. Gas flow from the gas insufflator 24 may be controlled by a preset gas pressure limit set on the insufflator device 24. For example, the pressure limit on the insufflator may be set to 25 mm Hg. The insufflator generally has a built-in pressure monitor, and it only instills gas when the detected pressure is below the limit. However, the insufflator pressure limit may be changed to a lower value or threshold. For instance, the pressure value may be set to 20 mm Hg if a patient cannot tolerate a limit set at 25 mm Hg.

The apparatus 100 generates output data based upon the detected pressure of gas instilled into the patient from the insufflator 24. A scan may be conducted when a relatively steady colonic pressure at a suitable level is detected such as at point 530 of FIG. 5. If a patient's colonic pressure exceeds a preset limit or threshold as defined on the insufflator device, the insufflator device will stop the flow of gas. On the other hand, if a patient's colonic pressure exceeds a second present limit as entered in input 73, the patient may need to be vented or some other form of intervention administered. When a patient is vented, gas is temporarily removed from the patient's colon to permit the colonic pressure to decrease to a more tolerable level. For example, a patient's colon typically has a resting pressure of 10 mm Hg. By venting the patient, the pressure may begin to return to the normal resting state. For example, if a patient is unable to tolerate a gas insufflator 24 setting of 25 mm Hg because of pain or discomfort, a setting of 20 mm Hg setting may then be used to attempt insufflation. Consequently, the second pressure limit prescribed in the input 73 may need to be lowered to reflect a different colonic pressure that would initiate intervention. A third preset (indicative of a dangerously high pressure condition), may also be prescribed in input 73. The third preset limit may be a threshold at which a patient's colonic pressure may rise to a threshold between 60 mm Hg and 100 mm Hg or even higher. If the third preset limit is reached, the patient would require immediate intervention such as rapid, automated venting.

The colonic pressure is detected by the gas pressure transducer 60. The detected pressure may spike when a patient is turned from one side to another side, such as from a supine position (patient on his or her back) to a prone position (patient on his or her stomach). Additionally, contractions may cause the colonic pressure to spike.

Figure 3:
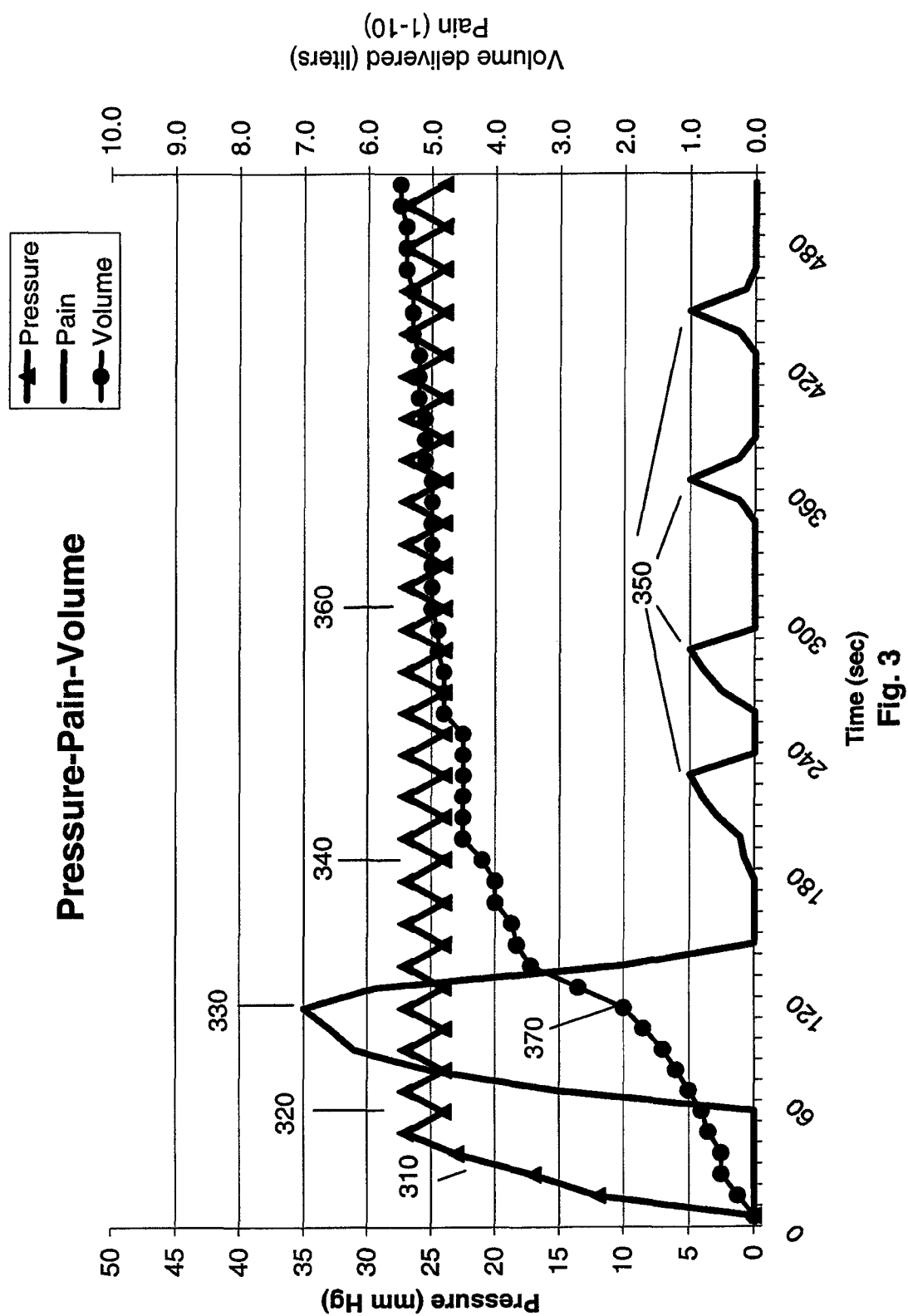
FIG. 3 is an exemplary chart of a hypothetical representation of patient pain, colonic pressure, and volume of gas delivered to a patient in accordance with the present invention.

Turning to FIG. 5, if a patient's colonic pressure is too low for too long, a reading may indicate that a gas leak is present or that gas is entering the small bowel. In FIG. 5, number 510 depicts a situation where the patient's colonic pressure may remain too low for too long and consequently a scan might be considered invalid. A rapid decrease in pressure during insufflation, such as at point 540, may indicate that the patient has expelled the rectal catheter 44, and the pressure returns to atmospheric pressure. A rapid decrease in colonic pressure may indicate that the time to start a scan is invalid, or if it occurs during a scan it may indicate that a scan is invalid. If colonic pressure readings indicate that the patient has a relatively quiescent period of colon activity, a scan may be performed such as at segments 530 and 560. For instance, if colonic pressure remains steady for approximately 15 seconds before the start time of a scan, a scan may be considered valid and hence performed. FIG. 3 depicts at 310 colonic pressure rising to approximately 25 mm Hg after approximately a minute, which is above a threshold of 20 mm Hg and below a threshold of 30 mm Hg 310. The colonic pressure is maintained at a steady level throughout insufflation at segments 320, 340, and 360 as shown in FIG. 3. Generally, the colonic pressure reading may range from 0 to 200 mm Hg. In one configuration, a selected time to conduct a scan occurs when pressure in the colon is approximately 25 mm Hg, a minimum volume of gas has been delivered, and the patient is relatively pain free. For this purpose, the gas insufflator 24 may be preset to allow the colonic pressure to reach 25 mm Hg. In another embodiment, the colonic pressure may be reduced to approximately 20 mm Hg to decrease patient discomfort but still adequately distend the patient's colon.

Colonic pressure may increase due to the presence of contractions in the patient's colon. Pain may correlate with bowel contractions, both of which are undesirable during a scan. Exaggerated contractions, or spasm, can be depicted on a chart of colonic pressure as one or more spikes such as 520 shown in FIG. 5. If the colonic pressure exceeds a preset value or threshold, the insufflator 24 stops administering gas to the patient. Accordingly, the flow rate will drop to 0 liters/minute. Generally, when the strip chart shows an increased amount of colonic pressure, the patient may experience discomfort or pain which may be reflected in the pain recording. However, the patient may experience variations in colonic pressure but not experience discomfort or pain. Variations in colonic pressure without pain may be due to each patient's pressure and/or pain tolerance threshold.

The processor 80 also processes data indicating the volume of gas delivered to the patient. Specifically, the processor 80 calculates the volume of gas administered based upon data reflecting rate of gas flow. The rate of gas flow is measured by the gas flow meter 70. Generally, the flow meter 70 may be set to "0" before an insufflation procedure. Data reflecting gas flow may be sent to the processor 80 from the flow meter 70. The processor 80 (or DAQ 86) calculates the volume of gas administered by integrating the rate of gas flow dispensed from the insufflator 24 with the length of time gas has been dispensed by the insufflator. By integrating the gas flow rate and the time elapsed, the processor 80 can calculate the volume of gas administered. Once the processor 80 calculates the volume of gas dispensed, the data may be plotted and displayed on a display 90. Generally, a scan may be started if a minimum amount of gas has been delivered to a patient. In one embodiment, 2 liters of gas may be too little of an amount of gas required to distend the colon, and hence represent a lower threshold. In another embodiment, 6 liters of gas may be too much gas administered to a patient and may for example represent an upper threshold.

If too much time has passed during which the patient has received less than a minimum amount of gas (for example, 2 liters), then problems may be present and the patient should not be scanned. On the other hand, if the technologist or physician determines that no technical problems exist and that only an amount of gas can be administered that is below a defined amount, then a scan may be performed to identify patient-related problems, such as an obstructing mass in the colon. In FIG. 6 at number 610, too little gas has been administered after 120 seconds and a scan conducted at this point may be considered to be invalid. For instance, if the technologist experiences difficulty in administering more than 2 liters of gas to the patient before starting a scan, an obstructing mass may be present in the colon which limits colonic distention. Alternatively, an obstruction in the tubing between the insufflator and the patient may limit the amount of gas administered. Also, the insufflator 24 may have been inadvertently been turned off or may be malfunctioning.

On the other hand, administration of approximately more than 6 liters of gas to the patient before starting the scan could also signal a problem. If too much gas is administered to a patient as at number 630 in FIG. 6, a scan may be considered invalid. For instance, gas may be leaking from the insufflator 24 or the tubing 22, 42. Gas may also be leaking from the patient if a seal is not established between the rectal catheter 44 and the patient. Alternatively, gas may reflux into the small intestine of the patient. In such an instance of gas entering the small bowel, a vasovagal response may occur. If the small bowel fills with gas, the patient may be at risk for experiencing a vasovagal response. For example, at number 620 in FIG. 6, the data shows that gas was delivered to a patient too quickly, perhaps resulting in small bowel distention that may lead to a vasovagal response. Typically when a patient experiences a vasovagal response, the patient may become cold, clammy and/or may lose consciousness. If any such clinical signs are exhibited by a patient, gas flow to the patient should be stopped and the patient's colon should be vented so the bowel pressure may be immediately reduced. Once the vasovagal symptoms subside, the insufflator 24 may be restarted. In one configuration, the vasovagal response may be avoided by an automated process of signaling the technologist that conditions are developing that might provoke a vasovagal response and that the patient may require manual or automated venting. Automated venting may include venting of the patient without signaling the technologist and having to wait for the technologist to make a decision (i.e., a form of computer-aided diagnosis and intervention).

The processor 80 communicates with the pain transducer 62, the gas pressure transducer 60, and the flow meter 70 and generates an output reflecting at least one or more of the output parameters, or an integrated function or some other mathematical function of such parameters. Typically, each output parameter has a threshold at which a scan may be performed. The processor 80 and the pain transducer 62 are calibrated to establish a pain scale of 0 to 10, wherein each increment is indicative of a degree of pain. A pain threshold may be established at a selected level such as approximately "2." However, since each patient's pain threshold varies, the pain threshold may be set at a different value. The gas pressure transducer 60 and the processor 80 communicate to indicate pressure within the patient's colon. A threshold may be established so that pressure in a patient's colon is detected at a threshold between 20 mm Hg and 30 mm Hg. The colonic pressure may be detected outside this threshold, particularly if the patient experiences contractions. Other threshold limits of pressure may be set, such as a dangerously high threshold. The processor may also generate an output reflecting volume of gas delivered to the patient. Typically, 2 to 6 liters of gas may be delivered during a VC procedure. However, if during the course of a scan more or less gas is delivered (or if contractions occur as manifested by pressure spikes), this may signal the need for rapid inspection of the scan image data by the doctor to determine if immediate, repeat scanning is necessary in order to prevent the study from being declared non-diagnostic and/or which might require the patient having to return at a later date for a repeat examination. However, in other situations and applications different amounts or volumes of gas may be administered and different threshold limits set.

Parameters indicative of colonic pressure, volume of gas delivered to a patient's bowel, and perceived patient pain may be detected at selected thresholds to determine whether a medical procedure such as a scan should be conducted. The parameters detected and/or calculated may be used to validate or invalidate a scan of a patient. For an example of parameters to validate or invalidate a patient scan, see FIG. 3. A threshold of gas volume to be delivered may be set at 2 liters for example. The volume of gas delivered increases over the first 180 seconds of the insufflation procedure. After approximately 120 seconds, 2 liters of gas have been administered to the colon as shown in FIG. 3 at number 370. As the volume of gas delivered to the bowel increases, the colonic pressure also increases. The colonic pressure increases over the first 60 seconds of the insufflation procedure as shown at number 310. The colonic pressure plateaus after approximately one minute and remains steady and quiescent throughout the rest of the procedure as shown at numbers 320, 340 and 360. Steady colonic pressure may be used to validate a scan. Perceived patient pain is also represented in the chart. The patient experiences a pain spike, as reflected by a squeeze on the bulb 35, colonic pressure has plateaued but while the volume delivered continues to increase as shown at number 330. A spike in pain may invalidate a scan such that a signal is produced indicating that undesired conditions exist, and hence the scan should not be started, or if the scan is already in progress, then the scan may be stopped. For instance, the pain threshold may be established as a "2" and the pain spike may be detected as a "7" magnitude. As the pain subsides at about 150 seconds, the scan may proceed with only minor discomfort indicated at number 350. If the pain persists or reaches a certain level, then intervention may be required. Episodes of minor discomfort may be detected by the pain transducer 60, again in response to a lighter squeeze of the bulb 35, as a "1" on the pain scale 350, but this is below a selected threshold of 2. When the bulb 35 is completely released, the pain drops to "0."

A patient may be prepared for a scan during the first 180 seconds as the three parameters stabilize. Patient scan preparation may involve some initial insufflation while the technologist prescribes scan parameters on the CT or MRI scanner console. Once the patient is prepared, a scan may be run after approximately 180 seconds. The scan may be started since no pressure spikes are detected for approximately 15 seconds, the patient is not experiencing any significant pain and more than 2 liters of gas have been administered to the patient's bowel. The lack of pain for 15 seconds, administration of at least 2 liters of gas, and stable colon pressure may validate a scan of a patient. Towards the end of the insufflation procedure, the colonic pressure remains quiescent and the patient may experience only minor discomfort. The total volume of gas delivered to the patient may be detected by the flow meter 70 as approximately 5 to 6 liters. However, alternate thresholds may also be utilized when desired. Depending on the speed of the scanner, the study may be terminated sooner than what is depicted in FIG. 3. For instance, a multi-detector CT scanner is capable of scanning a patient's colon in approximately 10 seconds which may cause the study to end sooner than depicted.

Although FIG. 3 depicts a chart combining all three parameters, each parameter may be depicted on a separate chart. Additionally, each parameter may not follow the trends depicted in FIG. 3. Turning to FIG. 4, for example, variations in pain are depicted. The patient does not perceive pain at the start of the insufflation procedure. The processor 80 may have been calibrated to detect a pain threshold of "2." The threshold is indicated by points 490 along the chart. After about 30 seconds, the pain input detector 34 detects a pain spike as shown at 410. The pain spike 410 is indicative of a high magnitude of pain perceived by the patient which is above the level 2 threshold. Since the pain resolves quickly, intervention may not be required. However, the pain spike may invalidate the start of a scan or the scan itself if it occurs during the scan. Following the pain spike, the perceived pain detected again exceeds the selected threshold at about 120 seconds, but again for only a short time. Once the pain has resolved and a steady state below threshold is maintained for a selected time, a scan may be run, for example, such as between 420 and 430. Perceived pain below a selected threshold may indicate minor discomfort due to bloating or tenesmus caused by distention of the patient's colon. Pain detected below the threshold may be used to validate a scan. The scan should not be performed when the patient's perceived pain fluctuates above the threshold of "2" following point 430. The patient may experience pain above a threshold for greater than a selected length of time and may require intervention. The patient may experience pain for longer than 5 seconds and may need to be vented or have some form of pharmacologic agent administered in order to decrease gas pressure and/or decrease perceived patient pain, respectively. Once the pain subsides, the technologist or physician may decide to restart the insufflation procedure. If pain persists above a certain threshold, the patient may be vented manually by the technologist or the patient may undergo automated venting or pharmacological intervention may be administered.

Variations in colonic pressure are depicted in FIG. 5. Typically a person's bowel maintains a resting pressure of approximately 10 mm Hg. For purposes of an insufflation procedure, a threshold may be established between 20 and 30 mm Hg. A lower threshold is indicated in FIG. 5 as points 590 along the chart. A second threshold may also be established. The second threshold is indicated in FIG. 5 as points 580 along the chart. A third threshold may also be provided to indicate a threshold such as between 60 mm Hg and 100 mm Hg at which automated venting would occur. In another example, the third threshold may be provided as a threshold above 100 mm Hg. Optionally, the apparatus 100 includes an electronically controlled release valve 185 which is automatically activated once the third threshold is reached. Once gas has been administered to the patient, the colon pressure should desirably be maintained at a steady state within the threshold limits and may be used to validate a scan such as at 530. The patient may also show minor fluctuations in pressure such as 560. If, on the other hand, the patient's colon does not reach a minimum threshold pressure, problems may exist and a scan may be invalidated, for example, as shown at 510. A low pressure reading may indicate a gas leak or it may indicate that the patient's small bowel in addition to the colon is filling with gas (if such condition is prolonged over time). If the gas pressure transducer 60 detects a rapid decrease in pressure during insufflation, the patient may have expelled the rectal catheter 44 as depicted at 540, or may have developed a leak in the tubing 42, 22. In another situation, a pressure reading reflecting fluctuations or spikes may indicate the patient is experiencing bowel contractions (including normal peristalsis or abnormal spasm) such as 520 and 550. A scan should not be performed if the pressure value is displayed on a chart as spikes such as at 520 that exceed a selected upper threshold at all or for a selected period of time. The spike at 550 indicates a contraction and a scan should not be started. Also, a scan should not be performed if colonic pressure is detected above a selected maximum threshold. As noted above, the third threshold may indicate that the patient's colon is reaching a dangerously high pressure value, such as between 60 mm Hg and 100 mm Hg. Rapid intervention may be necessary to relieve the pressure in the patient's colon.

Turning to FIG. 6, volume of gas delivered to the patient's colon as derived from the integral of flow and time is depicted. A threshold may be set so that an acceptable level of gas delivered is between 2 and 6 liters of gas. A medical procedure such as a scan may be conducted upon administration of a minimum of 2 liters of gas. In one instance, 2 liters of gas should be supplied to the patient within the first few minutes of insufflation. Administration of 2 liters of gas within the first few minutes may indicate a scan is valid. Several situations may arise when a scan is invalidated. For instance, the patient may have too little gas administered within the first 2 minutes such as at 610. On the other hand, gas should not be delivered to the patient's colon too rapidly such as at 620. If the processor 80 calculates that too much gas is delivered to the patient too quickly, this may be an indication that gas may be leaking or filling the patient's small bowel. When gas fills the small bowel, the patient is at risk of experiencing a vasovagal response. If too much gas is delivered to a patient such as at 630, gas may be leaking from the patient or from the tubing connecting the patient with the insufflator 24. The delivery of too much gas may also indicate that gas is filling the small bowel, and the patient is at risk for a vasovagal response. A signal may be generated when too much gas has been administered, however the administration to too much gas does not necessarily invalidate a scan. The appropriate volume of gas administered to a patient may be determined based on an analysis of certain patient parameters such as body mass index (BMI). This information may also be used to validate or invalidate a scan.

In summary, a scan may be started once certain conditions are satisfied. For example, in FIG. 3, a scan may be started once the patient does not perceive significant pain for a period of time preceding the start of the scan, once the colonic pressure has stabilized at a sufficient level, and after a minimum amount of gas has been administered, as shown at number 340. The pressure of the patient's colon appears to be steady such that a constant pressure plateau has been reached. Colonic pressure is shown to be steady in FIG. 3 commencing at numbers 310 and continuing thereafter at 320, 340 and 360. If the plateau is not reached in the span of 1 minute, an increased likelihood exists that the insufflator 24 should be adjusted or that the patient is not properly receiving gas. A steady pressure of gas at a desired level in the patient's colon reflects that a relatively quiet period of bowel activity has been reached. An example of a quiet period of bowel peristalsis might be that no pressure spikes are detected for approximately 15 seconds preceding the start of a scan.

In a selected application, the scan of the patient may take only a short amount of time. In the case of short scan times, generally the patient scan is completed even if undesirable parameters may be obtained mid-scan. Accordingly, the scan is generally permitted to finish instead of stopping mid-scan. Other types of scans may take 60 seconds or more to scan a patient. However, if the technologist sees undesirable readings as the patient is scanned, the scan may be stopped. For example, if the output shows that the patient has experienced significant pain or contractions occurred during the scan, the scan may need to be repeated. The pain event or the contraction event may be depicted as a spike in the patient pain reading or the colonic pressure reading, respectively, and may signal the need for immediate review of the scan image data by the technologist or doctor to determine the validity or accuracy of the scan data. If contracted or collapsed segments of bowel are identified, then the scan may need to be repeated.

It may be undesirable to conduct a scan if certain conditions are present. For instance, any significant pain perceived by the patient is undesirable. If a patient experiences pain, the patient may breath, squirm or move while the scan is performed, thereby leading to image artifacts and inaccurate results. During a scan, the patient is required to hold his or her breath while the scan is performed. Movement of the abdomen and diaphragm may create respiratory motion artifacts in the scan image data which can mimic or mask abnormalities. If a scan is performed while the patient experiences significant pain, the patient may also breathe inadvertently, thereby yielding inaccurate results. Accordingly, it is preferable to run the scan when the patient is relatively pain free in order to minimize or prevent motion artifacts, including respiratory motion artifacts.

In a selected configuration, apparatus 100 may be automated. For instance, the processor 80 may regulate the amount and/or rate of gas delivered to the patient. The processor 80 can be programmed with one or more preset values for gas pressure and pain tolerances. For example, if the patient experiences distress, the input sensor 35 will signal the pain transducer 62 and then the processor 80 that the patient is experiencing pain, cramping or discomfort. The processor 80 may thereby signal the need for intervention, including venting the patient and/or pharmacologic intervention. Venting the patient may include having the technologist manually disconnect the tubing 22 or by having the processor 80 activate an automated pressure release valve such as an electronically controlled release valve 185. Automated computer analysis of the pain, pressure and/or flow waveforms can also be used to signal validity of parameters within a selected threshold so that scanning of the patient's colon may begin.

The instant application may be used in other applications. For instance, the apparatus can be used as a diagnostic tool, with or without a concomitant scanning procedure, for the diagnosis of and determination of treatment efficacy for certain diseases such as irritable bowel syndrome (IBS). By simultaneously measuring colonic pressure, perceived patient pain, and/or volume of gas in the colon, diseases such as IBS, colonic dysmotility, and other such diseases and conditions may be studied. The apparatus 100 can be used as a diagnostic tool even though a patient scan is not required. For instance, the apparatus 100 may be used to determine physiological and sensory parameters of a patient regardless of whether a patient is scanned. Accordingly, a device which provides detailed information concerning a patient's bowel physiologic state, such as degree of colonic distention, coupled with perceived patient sensations, such as pain, would be a useful tool in diagnosing and treating such diseases.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

The invention claimed is:

1. An apparatus configured to provide a representation indicative of a scanning condition of a patient's colon, the apparatus comprising:

a pressure transducer configured to detect a pressure level of gas within a patient's colon and to generate an output indicative of the pressure level of gas detected;
a flow meter configured to detect a volume level of gas delivered to the patient's colon and to generate an output indicative of the volume level of gas detected;
a visual display;
a processor in communication with the pressure transducer, the flow meter, and the visual display;
circuitry in communication with the processor, wherein the circuitry is configured to monitor a period of time over which the pressure level is detected and maintained within a predetermined range of pressures; and
a sensory transducer configured to detect a patient's pain level and to generate an output indicative of the pain level detected,
wherein the processor is configured to receive the outputs from the pressure transducer the flow meter, the circuitry, and the sensory transducer and to cause the visual display to present a representation of at least one of the pressure level or the volume level detected within the patient's colon and the pain level detected.

2. The apparatus of claim 1, wherein the processor is configured to receive an input from a user that indicates a desired range of the pressure level of gas within the patient's colon.

3. The apparatus of claim 1, wherein the processor is configured to receive an input from a user that indicates a threshold volume level of gas delivered to the patients colon.

4. The apparatus of claim 1 further comprising a signaling unit that generates an indication to a user in response to detection of a predetermined pressure level and volume level.

5. The apparatus of claim 4, wherein the indication provided by the signaling unit comprises at least one of an electronic signal, an alarm, a flashing light, or a sound alarm.

6. The apparatus of claim 1, wherein the representation presented by the visual display comprises plotted data of at least one of the pressure level or the volume level over time.

7. The apparatus of claim 1, wherein at least one of the outputs is stored for further use by a user.

8. The apparatus of claim 1, wherein the processor is further configured to determine that the pressure level is within a predetermined range of pressures for a predetermined period of time in an instance in which the pressure level is within the predetermined range of pressures for the predetermined period of time and that the volume level meets a predetermined threshold volume level in an instance in which the volume level meets the predetermined threshold volume level.

9. A method for providing a representation indicative of a scanning condition of a patient's colon comprising:
insufflating a patient's colon with gas;
detecting, via a pressure transducer, a pressure level of the gas within the patient's colon;
generating, via the pressure transducer, an output indicative of the pressure level detected;
detecting, via a flow meter, a volume level of gas delivered to the patient's colon;
generating, via the flow meter, an output indicative of the volume level detected;
monitoring, via a circuitry in communication with the processor, a period of time over which the pressure level is detected and maintained within a predetermined range of pressures;
detecting, via a sensory transducer, a pain level of the patient;

generating, via the sensory transducer, an output indicative of the pain level detected;

receiving, via a processor in communication with the pressure transducer, the output indicative of the pressure level detected;

receiving, via the processor in communication with the flow meter, the output indicative of the volume level detected;

receiving, via the processor in communication with the sensory transducer, the output indicative of the pain level detected; and presenting, via a display in communication with the processor, a representation of the pain level detected and at least one of the pressure level detected or the volume level detected over time.

10. The method of claim 9 further comprising receiving an input from a user that indicates a desired range of the pressure level of gas within the patients colon.

11. The method of claim 9 further comprising receiving an input from a user that indicates a threshold volume level of gas delivered to the patient's colon.

12. The method of claim 9 further comprising generating, via a signaling unit, an indication to a user in response to detection of a predetermined pressure level and volume.

13. The method of claim 12, wherein the indication provided by the signaling unit to the user comprises at least one of an electronic signal, an alarm, a flashing light, or a sound alarm.

14. The method of claim 9, wherein the representation presented via the display comprises plotted data of at least one of the pressure level or the volume level over time.

15. The method of claim 9 further comprising storing at least one of the outputs for further use by a user.

16. The method of claim 9 further comprising:

determining, via the processor in communication with the pressure transducer, that the pressure level detected is within a predetermined range of pressures for a predetermined period of time in an instance in which the pressure level is within the predetermined range of pressures for the predetermined period of time; and determining, via the processor in communication with the pressure transducer, that the volume level detected meets a predetermined threshold volume level in an instance in which the volume level meets the predetermined threshold volume level.

* * * * *